United States Patent
Gordon et al.

(10) Patent No.: US 10,524,711 B2
(45) Date of Patent: Jan. 7, 2020

(54) COGNITIVE EVENT PREDICTOR

(71) Applicant: INTERNATIONAL BUSINESS MACHINES CORPORATION, Armonk, NY (US)

(72) Inventors: Michael S. Gordon, Yorktown Heights, NY (US); James R. Kozloski, New Fairfield, CT (US); Peter K. Malkin, Ardsley, NY (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 505 days.

(21) Appl. No.: 14/299,698

(22) Filed: Jun. 9, 2014

(65) Prior Publication Data

US 2015/0351680 A1 Dec. 10, 2015

(51) Int. Cl.
*A61B 5/16* (2006.01)
*A61B 5/00* (2006.01)
(Continued)

(52) U.S. Cl.
CPC .............. *A61B 5/162* (2013.01); *A61B 5/165* (2013.01); *A61B 5/7275* (2013.01); *G06F 19/00* (2013.01);
(Continued)

(58) Field of Classification Search
CPC ....... A61B 5/162; A61B 5/165; A61B 5/7275; A61B 5/7282; A61B 5/7285; A61B 5/7289
See application file for complete search history.

(56) References Cited

U.S. PATENT DOCUMENTS 7,547,279 B2 * 6/2009 Kim .................... A61B 5/02405
128/920
7,653,605 B1 1/2010 Jackson
(Continued)

FOREIGN PATENT DOCUMENTS

EP 2660745 A2 11/2013
WO 2012025622 A2 3/2012

OTHER PUBLICATIONS

List of IBM Patents or Patent Applications Treated as Related, Sep. 24, 2014, pp. 1-2.
(Continued)

*Primary Examiner* — Devin B Henson
*Assistant Examiner* — H. Q. Nguyen
(74) *Attorney, Agent, or Firm* — Law Office of Jim Boice

(57) ABSTRACT

A method and/or computer program product identifies and/or predicts a cognitive state of a user. A buffer on a device is loaded with a predetermined set of sensor readings for a user. A hardware receiver receives a "push" signal from the device. The "push" signal is transmitted by the user in response to the user subjectively experiencing a user-defined cognitive state. The "push" signal causes readings from the buffer to be loaded as pushed sensor readings onto a data matrix. One or more processors analyze the pushed sensor readings to identify a sensor pattern of the pushed sensor readings. In response to detecting a subsequent set of sensor readings that match the sensor pattern of the pushed sensor readings, a signal transmitter transmits a cognitive state signal that indicates a prediction of a particular cognitive state of the user.

7 Claims, 4 Drawing Sheets

(51) Int. Cl.
*G16H 50/20* (2018.01)
*G06F 19/00* (2018.01)
*G16H 50/30* (2018.01)
*A61B 5/0205* (2006.01)

(52) U.S. Cl.
CPC ............ *G16H 50/20* (2018.01); *A61B 5/0004* (2013.01); *A61B 5/0205* (2013.01); *A61B 5/4803* (2013.01); *A61B 5/681* (2013.01); *A61B 2560/0242* (2013.01); *G16H 50/30* (2018.01)

(56) References Cited

U.S. PATENT DOCUMENTS

| | | | |
|---|---|---|---|
| 7,788,208 B2 | 8/2010 | Kobayashi et al. | |
| 7,874,983 B2 | 1/2011 | Zancho et al. | |
| 8,108,033 B2* | 1/2012 | Drew | A61B 5/0006 600/509 |
| 8,412,665 B2 | 4/2013 | Wang et al. | |
| 2001/0031930 A1 | 10/2001 | Roizen et al. | |
| 2005/0277813 A1 | 12/2005 | Katz et al. | |
| 2009/0002178 A1* | 1/2009 | Guday | A61B 5/0002 340/573.1 |
| 2010/0217097 A1* | 8/2010 | Chen | A61B 5/16 600/301 |
| 2010/0324427 A1 | 12/2010 | Devot et al. | |
| 2011/0263946 A1 | 10/2011 | El Kaliouby et al. | |
| 2011/0301436 A1 | 12/2011 | Teixeira | |
| 2012/0029311 A1 | 2/2012 | Raptis et al. | |
| 2012/0289789 A1* | 11/2012 | Jain | A61B 5/4848 600/301 |
| 2013/0262182 A1 | 10/2013 | Kodra et al. | |
| 2015/0206053 A1* | 7/2015 | Hayden | G06N 5/02 706/46 |
| 2015/0226621 A1 | 8/2015 | Zhu et al. | |
| 2015/0305426 A1 | 10/2015 | Lee et al. | |

OTHER PUBLICATIONS

B. Sauser, "A Helmet That Detects Hard Hits", MIT Technology Review, Sep. 10, 2007, pp. 1-2.

A.A. Abdullah, et al., "Design and Development of an Emotional Stress Indicator (ESI) Kit", IEEE, IEEE Conference on Sustainable Utilization and Development in Engineering and Technology (STUDENT), 2012, Kuala Lumpur, pp. 253-257 (Abstract Only).

Fitbit, Inc., "Make Fitness a Lifestyle With Flex (TM)", Fitbit, Inc., <www.fitbit.com/flex>, Retrieved Jun. 6, 2014, pp. 1-7.

U.S. Appl. No. 14/328,349 Non-Final Office Action dated Aug. 11, 2016.

U.S. Appl. No. 14/328,349 Final Office Action dated Jul. 7, 2017.

* cited by examiner

COGNITIVE EVENT PREDICTOR

BACKGROUND

The present disclosure relates to the field of computers, and specifically to the use of computers in evaluating cognitive states. Still more particularly, the present disclosure relates to predicting a specific cognitive state of a particular user based on sensor(s) readings for the particular user.

A person's cognitive state is also known as a person's "state of mind". This state of mind may be normal (e.g., interested, sleepy, asleep, alert, bored, curious, doubtful, etc.), or it may be indicative of some type of pathology (e.g., amnesia, confusion, panic, etc.). Often, such states of mind will manifest themselves measurably before a person realizes that he/she is entering such a state of mind.

SUMMARY

In one embodiment of the present invention, a method and/or computer program product identifies and/or predicts a cognitive state of a user. A buffer on a device is loaded with a predetermined set of sensor readings for a user. A hardware receiver receives a "push" signal from the device. The "push" signal is transmitted by the user in response to the user subjectively experiencing a user-defined cognitive state. The "push" signal causes readings from the buffer to be loaded as pushed sensor readings onto a data matrix. One or more processors analyze the pushed sensor readings to identify a sensor pattern of the pushed sensor readings. In response to detecting a subsequent set of sensor readings that match the sensor pattern of the pushed sensor readings, a signal transmitter transmits a cognitive state signal that indicates a prediction of a particular cognitive state of the user.

In one embodiment of the present invention, a Cognitive Event Predictor (CEP) wearable device comprises: a set of one or more sensors, wherein the one or more sensors are configured to detect, record, and quantify a physical event associated with a user; a set of continuous circular buffers for storing a first set of sensor readings from the one or more sensors; a hardware storage device for storing the first set sensor readings as a first matrix, wherein the first set of sensor readings are stored in the first matrix in response to the user subjectively experiencing a user-defined cognitive state; a hardware comparator for comparing the first matrix with a second matrix derived from a second set of sensor readings, wherein the second set of sensor readings are received after the first set of sensor readings; and a signal transmitter, wherein the signal transmitter transmits a signal indicating a prediction that the user-defined cognitive state will re-occur in the user in response to the user experiencing factors that caused the first and second set of sensor readings to be generated by the set of one or more sensors.

DETAILED DESCRIPTION

Figure 1:
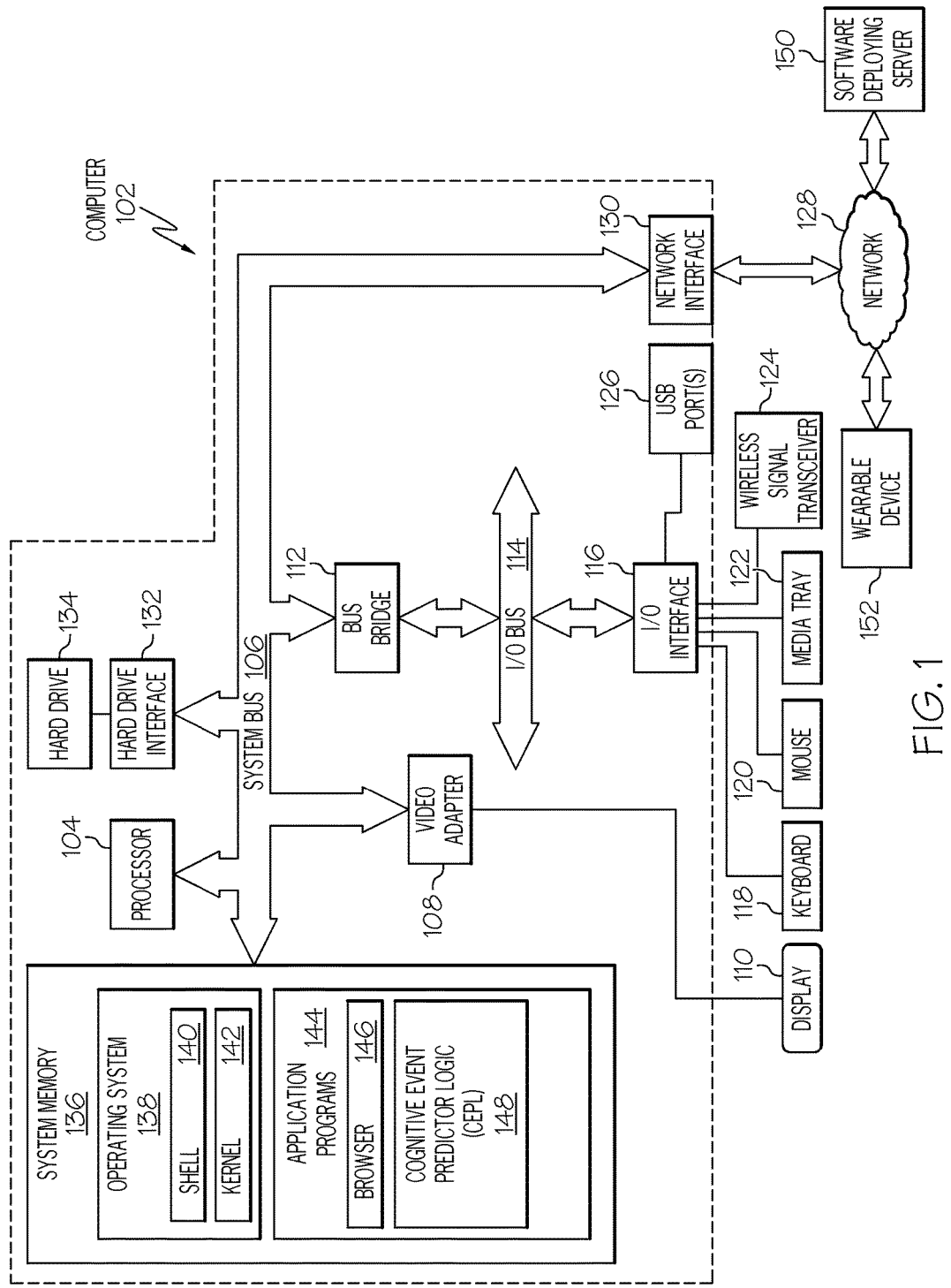
FIG. 1 depicts an exemplary system and network in which the present disclosure may be implemented.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

With reference now to the figures, and in particular to FIG. 1, there is depicted a block diagram of an exemplary system and network that may be utilized by and/or in the implementation of the present invention. Note that some or all of the exemplary architecture, including both depicted hardware and software, shown for and within computer 102 may be utilized by software deploying server 150 and/or a wearable device 152.

Exemplary computer 102 includes a processor 104 that is coupled to a system bus 106. Processor 104 may utilize one or more processors, each of which has one or more processor cores. A video adapter 108, which drives/supports a display 110, is also coupled to system bus 106. System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a wireless signal transceiver 124 (e.g., a near field radio frequency transceiver, a Wi-Fi transceiver, etc.), and external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150, using a network interface 130. Network interface 130 is a hardware network interface, such as a network interface card (NIC), etc. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other computer systems.

Application programs 144 in computer 102's system memory (as well as software deploying server 150's system memory) also include a Cognitive Event Predictor Logic (CEPL) 148. CEPL 148 includes code for implementing the processes described below, including those described in FIGS. 2-4. In one embodiment, computer 102 is able to download CEPL 148 from software deploying server 150, including in an on-demand basis, wherein the code in CEPL 148 is not downloaded until needed for execution. Note further that, in one embodiment of the present invention, software deploying server 150 performs all of the functions associated with the present invention (including execution of CEPL 148), thus freeing computer 102 from having to use its own internal computing resources to execute CEPL 148.

Note that the hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

As a high-level overview of one or more embodiments of the present invention, the present invention takes two steps. The first step is to identify certain user preconditions that occur before the user enters into a specific cognitive state. Thereafter (the second step), when this same user experiences these same preconditions, then a prediction is made that this user is (or will be) experiencing that specific cognitive state.

Figure 2:
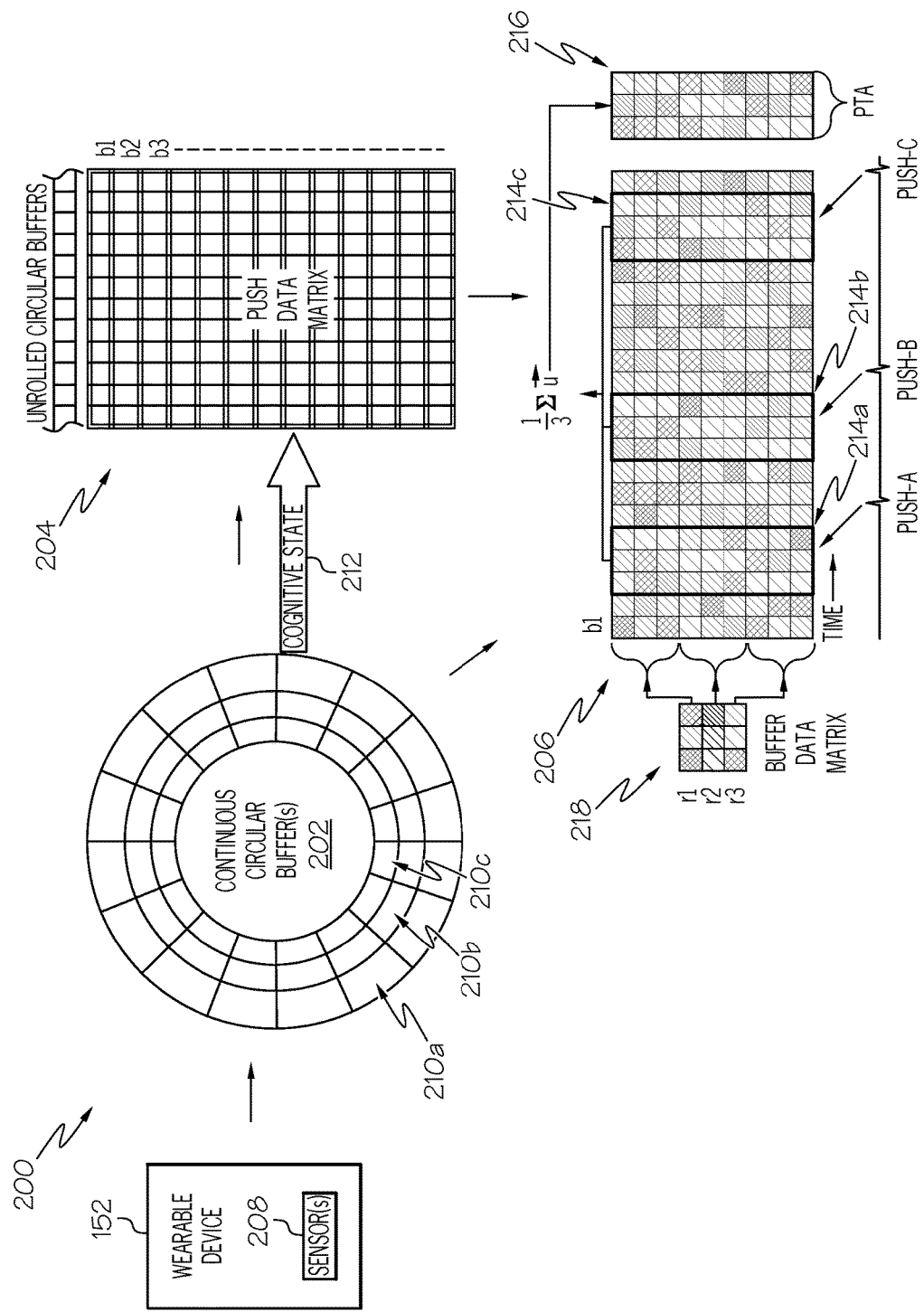
FIG. 2 illustrates an exemplary Cognitive Event Predictor (CEP) architecture in accordance with one or more embodiments of the present invention.

With reference now to FIG. 2, an exemplary Cognitive Event Predictor (CEP) architecture 200 is presented in accordance with one or more embodiments of the present invention. Note that the CEP architecture 200 and data generated by the CEP architecture is secret. That is, predictions of current or future cognitive states are presented only to the user that generated the sensor readings described herein and/or experiences the specific cognitive state that follows these sensor readings. Only with the express approval of the user will such readings/states be shared with others.

Note that in one embodiment the CEP architecture 200 also includes multiple components found in FIG. 1 (e.g., computer 102, wearable device 152, etc.). Furthermore, in one embodiment, the continuous circular buffer(s) 202, the push data matrix 204, and/or the accumulation data matrix 206 shown in FIG. 2 and/or components shown in FIG. 1 are all within the wearable device 152. In one or more other embodiments, the continuous circular buffer(s) 202 are within the wearable device, but the push data matrix 204 and/or accumulation data matrix 206 are stored in a hardware storage device (e.g., system memory 136 and/or hard drive 134 shown in FIG. 1) on a remote computer, such as computer 102 shown in FIG. 1.

Wearable device 152 includes one or more sensor(s) 208. In one embodiment, each of the sensor(s) 208 are "smart sensors", that include processing logic that is able to detect, record, and quantify what is being sensed. That is, each of the sensor(s) 208 is 1) able to detect a particular physical event (heat, noise, biometrics, etc.); 2) quantify the level of that particular physical event (e.g., how high the heat is, what the duration/intensity of the noise is, what the specific readings of the biometric is, etc.); 3) convert that level into a digital value; and/or 4) send that digital value to the continuous circular buffer(s) 202. In one embodiment, these functions are performed by dedicated hardware logic, which takes digital readings from the sensors, compares the digital readings to known ranges in order to establish the digital value, and then transmits (e.g., by a wireless digital signal transmitter) the digital value to the continuous circular buffer(s) 202, which then (responsive to a "push" signal from the user) send the stored digital values from the continuous circular buffer(s) 202 to a local matrix within the wearable device 152 or to a remote matrix in a remote computer (e.g., computer 102 shown in FIG. 1). In either embodiment, the system can use a near field network to send the digital value to a local storage within the wearable device 152, or to a remote device, such as a smart phone held by the user, or to a server on a cloud, etc. (e.g., using a Wi-Fi signal).

In one embodiment, sensor(s) 208 are physiological sensors, which are defined as sensors that are able to detect physiological states of a person. In one embodiment, these sensors are attached to the person via the wearable device 152. Example of such sensors include, but are not limited to, a heart monitor, a blood pressure cuff/monitor (sphygmomanometer), a galvanic skin conductance monitor, an electrocardiography (ECG) device, an electroencephalography (EEG) device, etc. That is, in one embodiment, the sensor(s) 208 are biometric sensors that measure physiological functions, of the wearer, which are not musculoskeletal.

In one embodiment, sensor(s) 208 detect and/or measure musculoskeletal bodily acts of the user, such as facial expressions (e.g., smiles, frowns, furrowed brows, etc.), body movements (e.g., walking gait, limps, stride length, stride speed, etc.), etc. Facial expressions may be detected by muscle movement sensors on eyeglasses, cameras on "smart glasses", etc. Body movements may be detected by motion detectors, stride counters, strain gauges in clothing, etc.

In one embodiment, sensor(s) 208 are speech content analyzers. In this embodiment, the sensor(s) 208 includes a speech-to-text converter, which then examines the text for certain keywords, speech pattern, etc. That is, the speech-to-text converter converts spoken words into written text, which can then be examined in order to identify certain predefined keywords. The presence (or absence) of such keywords is then used by logic (e.g. CEPL 148 in FIG. 1) to ascertain the nature of the speech, which may lead to a prediction of a future cognitive state of the user (as described herein).

In one embodiment, sensor(s) 208 are speech content analyzers. In this embodiment, the sensor(s) 208 includes a speech-to-text converter, which then examines the text for certain features. These features may include the construction of graphs representing structural elements of speech based on a number of alternatives, such as syntactic value (article, noun, verb, adjective, etc.), or lexical root (run/ran/running) for the nodes of the graph, and text proximity for the edges of the graph. Graph features such as link degree, clustering, loop density, centrality, etc., representing speech topological structure are also therefore included. Similarly, semantic vectors may be extracted from the text as features, using systems such as that provided by a Latent Semantic Analysis, WordNet, etc. These methods allow the computation of a distance between words and specific concepts (e.g. introspection, anxiety, depression), such that the text can be transformed into features representing a field of distances to a concept, a field of fields of distances to the entire lexicon, or a field of distances to other texts including books, essays, chapters and textbooks. The syntactic and semantic features may then be combined either as a "bag of features" or as integrated fields, such as the Potts model. Similarly, locally embedded graphs may be constructed, so that a trajectory in a high-dimensional feature space is computed for each text. This trajectory is used as a measure of coherence of the speech, as well as a measure of distance between speech trajectories using methods such as Dynamic Time Warping.

In one embodiment, sensor(s) 208 are speech inflection analyzers. In this embodiment, the sensor(s) 208 compare voice patterns with known voice patterns (pitch, timing, tremor, etc.) of the user, in order to identify certain emotions such as stress, relaxation, alertness, sleepiness, and other cognitive states. The presence (or absence) of such voice patterns is then used by logic (e.g. CEPL 148 in FIG. 1) to ascertain the current emotional state of the user, which may lead to a prediction of a future cognitive state of the user (as described herein).

In one embodiment, sensor(s) 208 are environmental sensors, such as an air thermometer, a microphone, a barometer, a light sensor, a moisture sensor, etc. In this embodiment, sensor(s) 208 are able to detect ambient (within the proximity of the user) environmental conditions, such as rain, various light levels, sound levels, air pressure, sound (e.g., noise, music, spoken words, etc.), etc.

As described herein, values stored in the continuous circular buffer(s) 202 are sent to the push data matrix 204 in response to the user initiating a "push" event. The "push" event occurs in response to the user subjectively experiencing a user-defined cognitive state. That is, as soon as the user "feels" that he/she is in a particular cognitive state, then he/she issues a "push" command, causing the contents of the continuous circular buffer(s) 202 to be loaded into the push data matrix 204.

Thus, in one or more embodiments of the present invention, sensor readings from sensor(s) 208 are buffered in the continuous circular buffer(s) 202. Continuous circular buffer(s) 202 are buffers that allow data to be stored in any location/cell within the buffer. Unlike a linear buffer (such as a First In First Out—FIFO buffer), a circular buffer allows "stale" data to be replaced with "fresh" data without shifting the location of existing data in other cells within the buffer. In one embodiment, continuous circular buffer(s) 202 is composed of multiple circular buffers 210a-210c (where "c" is an integer). In one embodiment, each of the circular buffers 210a-210c is devoted to storing readings from a specific sensor from sensor(s) 208.

For example, assume that circular buffer 210a is devoted to storing readings from a sensor 208 that measures a heart rate of the user. When data from circular buffer 210a is sent to push data matrix 204, it is stored in the unrolled buffer shown as b1. Assume further that circular buffer 210b is devoted to storing readings from a sensor 208 that measures an ambient light level where the user is located. When data from circular buffer 210b is sent to push data matrix 204, it is stored in the unrolled buffer shown as b2. Assume further that circular buffer 210c is devoted to storing readings from a sensor 208 that measures speech patterns of the user. When data from circular buffer 210c is sent to push data matrix 204, it is stored in the unrolled buffer shown as b3. Thus, readings from a particular sensor are stored in a particular circular buffer as well as a particular unrolled (linear) buffer in a buffer matrix.

Note that while the present disclosure presents continuous circular buffer(s) 202 as a single circle, other circular buffers having multiple interlocking circular buffers are contemplated as being within the scope of the present invention.

As described herein, data is sent from the continuous circular buffer(s) 202 to the push data matrix 204 in response to a "push" being initiated by the user when the user subjectively experiences a particular cognitive state. Note that in one embodiment, experiencing this particular cognitive state is purely subjective. That is, the particular cognitive state is subjective and unique to that user. For example, one user may experience the cognitive state of "alertness" when sensor(s) 208 detect a particular pattern of conditions (physiological, temporal, environmental, etc.). However, another user may experience the cognitive state of "boredom" when sensor(s) 208 detect this same particular pattern of conditions for this other user. Thus, each person responds differently to the same set/pattern of conditions.

As described herein, in response to experiencing a particular cognitive state, the user will initiate a "push" of data from the continuous circular buffer(s) 202 to the push data matrix 204, which is stored on a hardware storage device. As shown in FIG. 2, the cognitive state 212 is represented by a digital value that is sent to the push data matrix 204. This digital value identifies a particular cognitive state of the user that is defined by the user, such that precursive readings from the sensor(s) 208 are associated with a subsequent and specific user-defined cognitive state.

In one embodiment, the particular cognitive state that is associated with specific precursive events (detected by the sensor(s) 208) is described by the user's own words. In another embodiment, the particular cognitive state is selected from a menu or is otherwise predefined.

Figure 3:
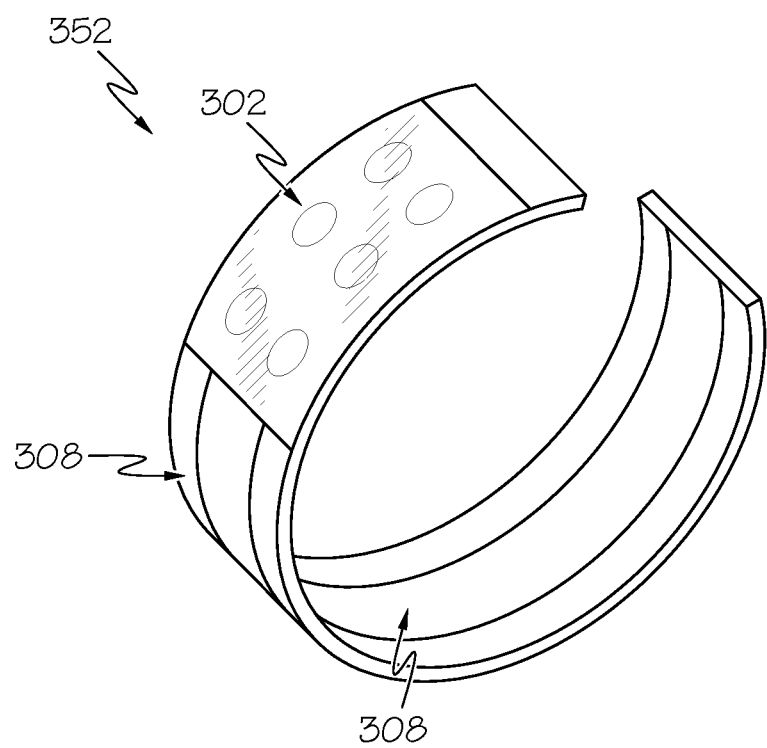
FIG. 3 depicts an exemplary wearable device for sensing user conditions and/or predicting a specific cognitive state of the user.

For example, consider the wearable device 352 depicted in FIG. 3. As shown, wearable device 352 (which may be worn on the wrist) includes a keypad 302. In one embodiment, keys on the keypad are pre-programmed for a particular cognitive state. For example, one of the keys may be for "boredom". Thus, if the user is experiencing "boredom", then the user pushing the button for "boredom" causes data from the continuous circular buffer(s) 202, along with a flag/signal that is associated with the cognitive state 212 for "boredom" (and identified by pushing the key on keypad 302 for "boredom"), to be sent to the push data matrix 204 in FIG. 2. Similarly, if the user is experiencing "anxiety", then data from the continuous circular buffer(s) 202, along with a flag/signal that is associated with the cognitive state 212 for "anxiety" (and identified by pushing the key on keypad 302 for "anxiety"), is sent to the push data matrix 204 in FIG. 2 when the user pushes the "anxiety" button on the keypad 302.

Note that wearable device 352 shown in FIG. 3 includes both biophysical (unique to the user) and ambient environmental sensors. More specifically, wearable device 352 includes sensors 308 that, depending on their structure, configuration, and/or positioning on the wearable device 352, are able to monitor biometric conditions (e.g., blood pressure, heart rate, etc.), musculoskeletalmotions (e.g., cameras that track a user's facial expressions, motion sensors that track a user's walking gait, etc.) and other biophysical features/conditions of the user, but also can track ambient environmental conditions (e.g., local sounds, light, moisture, air temperature, etc.).

Returning now to FIG. 2, assume that data from continuous circular buffer(s) 202 is continuously sent to accumulation data matrix 206. In this embodiment, accumulation data matrix 206 takes continuous readings from the continuous circular buffer(s) 202. However, each set of data that has been pushed to the push data matrix 204 is nonetheless identified within the accumulation data matrix 206. For example, data that was pushed to push data matrix 204 at the time of a "PUSH-A" is identified by block 214a; data that was pushed to push data matrix 204 at the time of a "PUSH-B" is identified by block 214b; and data that was pushed to push data matrix 204 at the time of a "PUSH-C" is identified by block 214c.

Data from blocks 214a-214c are then used to determine a Push Triggered Average (PTA), shown as push average matrix 216. Push average matrix 216 is calculated (e.g., by CEPL 148 shown in FIG. 1) as one-third (assuming that three pushes occurred) of the sum of the values stored in each cell of the pushed buffers. That is, assume that a push results in three columns of nine cells. The values in the upper left cell in each of the blocks 214a-214c are summed together, divided by three, and the quotient (i.e., average) is then stored in the upper left cell of the push average matrix 216. Other cells in the 214a-214c are similarly summed together, divided by three, and their quotients (i.e., averages) are then stored in the corresponding cell of the push average matrix 216. This PTA (push average matrix 216) is then used as a "fuzzy" reference for new values pushed from the continuous circular buffer(s) 202. That is, PTA (push average value 216) provides a mean average for each of the sensed parameters. Ranges around these mean values (above and below) are predetermined, such that when values from the continuous circular buffer(s) 202 later fall within these ranges, a prediction can be made that the user will again experience (or is currently experiencing) the user-defined cognitive state.

In one embodiment, a buffer data matrix 218 is generated from a single buffer in the push data matrix 204. For example, consider buffer b1 from push data matrix 204. Assume that buffer b1 contains data from continuous circular buffer 210a that describe the heart rate of the user who is wearing the wearable device 152. As depicted, b1 is broken down into three rows, r1-r3, in order to create the buffer data matrix 218. Buffer data matrix 218 is then used in a manner similar to that described herein for push data matrixes. That is, rather than require a push data matrix from multiple sensors, pushed (or alternatively, non-pushed but rather continuously streamed) data from a single sensor is converted into a matrix (buffer data matrix 218), which is then used to predict a particular cognitive state of the user by comparing this buffer data matrix 218 to known single-sensor data matrixes that are precursive to the particular cognitive state of the user.

Note that while, as the name suggests, wearable device 152/352 is presented as a wearable device, in one or more embodiments the wearable device 152/352 is a device that is simply proximate to, although not necessarily worn by, a user, such that ambient conditions, including biophysical traits of the user (e.g., frowns, smiles, flushed skin, etc.) are still sensed by sensors, such as sensors 208.

Figure 4:
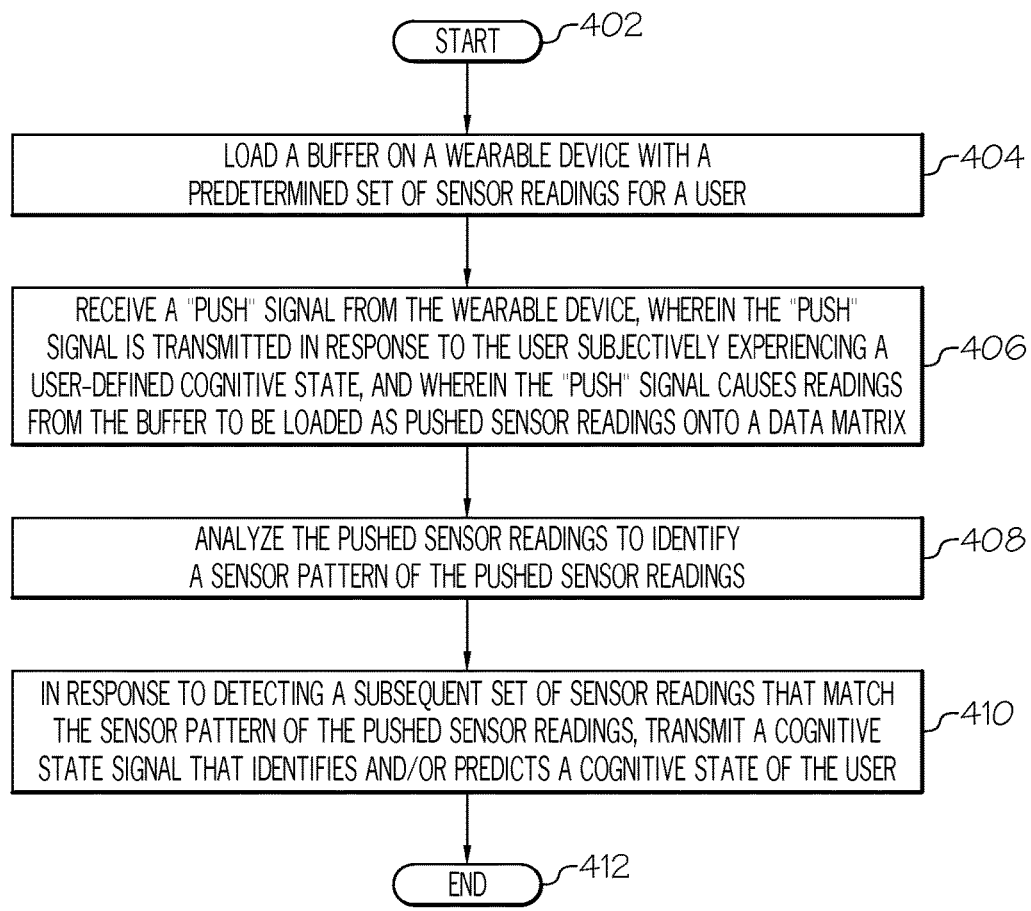
FIG. 4 is a high-level flowchart of one or more steps performed by one or more processors to identify and/or predict a cognitive state of a user.

FIG. 4 is a high-level flowchart of one or more steps performed by one or more processors to identify and/or predict a cognitive state of a user. After initiator block 402, a buffer (e.g., continuous circular buffer(s) 202 shown in FIG. 2) on a wearable device is loaded with a predetermined set of sensor readings (e.g., from sensor(s) 208 in FIG. 2) for a user, as described in block 404. Note that these sensor readings are unique and specific for the person who is wearing the wearable device (e.g., wearable device 352 shown in FIG. 3).

As described in block 404, a hardware receiver (e.g., the wireless signal transceiver 124 shown in FIG. 1, which may be a component of a wearable device such as the wearable device 352 shown in FIG. 3, or which may be a component in a monitoring computer, such as computer 102 shown in FIG. 1) receives a "push" signal from the wearable device. This "push" signal is transmitted by the user in response to the user subjectively experiencing a user-defined cognitive state. As described herein, the "push" signal causes readings from the buffer to be loaded as pushed sensor readings onto a data matrix.

Note again that the user-defined cognitive state is subjectively experienced. That is, the cognitive state (e.g., anger, happiness, alertness, tranquility, etc.) occurs when that particular user experiences events detected by the sensors (e.g., increased heart rate, flashing light, quiet sounds, the user speaking in a particular speech pattern, etc.). The present invention is premised on each user responding to the experienced events differently. That is, one person may respond to flashing lights, loud noise, an increase in his heart rate, and profuse sweating (sensed events) with heightened anxiety (a first cognitive state), while another person may respond to these same sensed events with a sense of tranquility (a second cognitive state). Therefore, it is up to the user to define his cognitive state, using the system described herein. The system will then determine what sensed events occurred before the user experienced the particular cognitive state. Note that while these sensed events are precursive (occur before the cognitive state in the user), in one or more embodiments of the present invention they are not causative (cause the cognitive state to occur in the user).

As described in block 408 in FIG. 4, hardware logic (e.g., processors) then analyze the pushed sensor readings to identify a sensor pattern of the pushed sensor readings. As described in FIG. 2, these patterns may be from data matrix patterns and/or linear buffer patterns, either of which are compared to known data patterns for this particular user.

As described in block 410 of FIG. 4, in response to one or more processors detecting a subsequent set of sensor readings that match the sensor pattern of the pushed sensor readings, a signal transmitter (e.g., wireless signal transceiver 124 shown in FIG. 1, which may be part of the wearable device or may be part of a monitoring computer system), then transmits a cognitive state signal that predicts a cognitive state of the user. This prediction may be that the user is currently experiencing the particular cognitive state, or that the user will experience this particular cognitive state in the future.

The flow chart ends at terminator block 412.

In one embodiment, the method further comprises loading the predetermined set of sensor readings onto continuous circular buffers, where each of the continuous circular buffers stores data from a different sensor in the wearable device. (See FIG. 2.) This allows the system to keep a continuous record of readings from the sensors, without disrupting the positions of other sensor readings. However, in an alternative embodiment, the predetermined set of sensor readings are loaded into a First In First Out (FIFO) linear buffer. By loading the sensor readings into a FIFO linear buffer, a relative (if not actual) temporal position of the readings can be established. That is, by loading sensor readings into a FIFO linear buffer, the system can recognize that the first sensor reading to be pulled off the FIFO linear buffer is the oldest, while the last sensor reading to be pulled off the FIFO linear buffer is the newest, relative to other readings stored in the FIFO linear buffer.

In one embodiment of the present invention, predicting whether a particular cognitive state will occur (or is presently occurring) is based on a Push Triggered Statistic (PTS), which uses statistical probability for determining the likelihood of a cognitive event occurring. In one embodiment, the PTS uses the probability formula:

$$P(M\mid E) = \frac{P(E\mid M)}{\sum_m P(E\mid Mm)P(Mm)} * P(M)$$

where:

P(M|E) is the probability that a specific cognitive state will occur (M) given that (|) data from the continuous circular buffers falls within a predefined Push Triggered Average (PTA) of previously pushed data from the continuous circular buffers;

P(E|M) is the probability that data from the continuous circular buffers falls within the predefined PTA of previously pushed data from the continuous circular buffers given that (|) the specific cognitive state is actually occurring (M);

P(M) is the probability that the specific cognitive state will occur regardless of any other information; and Σm is the sum of all occurrences m, for the probability P(E|M) (that is, P(E|Mm)) times the probability P(M) (i.e., P(Mm)).

Note that in one embodiment, various statistical methodologies can be used to predict a user's cognitive state based on sensor readings. For example, a first order or multiple order statistical analysis will compare previous sensor readings with current sensor readings. If the current sensor readings match the previous sensor readings within a statistically-satisfactory range (e.g., in a bell curve there is less than a standard deviation of 1 between the two sets of sensor data), then the current sensor readings will be presumed to lead to a same cognitive state as the previous sensors readings.

The following exemplary use case describes one or more embodiments of the present invention described herein. Sensors 208 within a wearable device 152, which the user is wearing, identify various physiological, biometric, and/or ambient environmental conditions surrounding or applicable to the user. These identified conditions are quantified and stored in the continuous circular buffer(s) 202. When the user subsequently senses that he/she is in a particular cognitive state (e.g., "alertness"), then he presses a button (e.g., from keypad 302 shown in FIG. 3) or otherwise activates the wearable device 152 (e.g., by squeezing the wearable device 152) to cause a "push". This push dumps the contents of the continuous circular buffer(s) 202 into a push data matrix 204 and/or an accumulation data matrix 206. Thereafter, new sensor data is generated by the sensor(s) 208. This new sensor data is streamed to a data matrix, such as the accumulation data matrix 206. If a pattern of sensor data matches that of sensor data that was sent from the continuous circular buffer(s) 202 by the "push", then a prediction is made that this user is, or soon will be, experiencing the cognitive state of "alertness".

Note further that in one embodiment, the user of the wearable device 152/352 has been trained to initiate a "push" operation whenever the user experiences one or more user-defined cognitive states. Thus, the user, and only the user, is in control of how the system records, analyzes, and interprets the sensor readings described herein. In one embodiment, this training is augmented by visual cues from the wearable device 152/352. For example, whenever the architecture described herein recognizes a pattern that suggests a cognitive state is actively occurring in the user, if the user has not initiated a "push" operation, the system may issue a query to the user, asking the user for his current cognitive state. Note that this query will not recommend any particular cognitive state. Thus, both the architecture and the user are trained. That is, the user is trained to recognize and report (using the "push" operation) any user-defined cognitive states, and the architecture is trained to recognize other cognitive states. For example, if the sensors 208 detect conditions that are predictive of cognitive state "A", but the user issues a "push" operation by indicating (e.g., using a button on the wearable device 152/352) that he/she is experiencing cognitive state "B", then the system will learn that the sensors readings are predictive of both cognitive state "A" and cognitive state "B" for that user.

Note that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A method comprising:
storing a first specific set of sensor readings from a first sensor that describe a physiological state of a user in a first circular buffer, wherein the first circular buffer is reserved for storing sensor readings from the first sensor;
storing a second specific set of sensor readings from a second sensor that describe a speech pattern of the user in a second circular buffer, wherein the second circular buffer is reserved for storing sensor readings from the second sensor;
storing a third specific set of sensor readings from a third sensor that describe an environment of the user in a third circular buffer, wherein the third circular buffer is reserved for storing sensor readings from the third sensor, wherein the first sensor, the second sensor, and the third sensor are components of a wearable device, and wherein the first, second, and third specific set of sensor readings are received during a first time period;
in response to the first sensor generating the first specific set of sensor readings, the second sensor generating the second specific set of sensor readings, and the third sensor generating the third specific set of sensor readings, prompting, by one or more processors, the user to input at least a first "push" signal on a pre-programmed key on the wearable device, wherein the first "push" signal includes a signal representing a current cognitive state of the user as identified by the user;
receiving, by a hardware receiver, the first "push" signal from the user of the wearable device, wherein the first "push" signal is transmitted by the user in response to the user subjectively experiencing the current cognitive state;

receiving a fourth specific set of sensor readings from the first sensor, wherein the fourth specific set of sensor readings are received at a second time period that is subsequent to the first time period;

receiving a fifth specific set of sensor readings from the second sensor, wherein the fifth specific set of sensor readings are received at the second time period;

receiving a sixth specific set of sensor readings from the third sensor, wherein the sixth specific set of sensor readings are received at the second time period;

comparing, by the one or more processors, the first, second, and third specific set of sensor readings to their respective fourth, fifth, and sixth specific set of sensor readings;

determining, by the one or more processors, that the first, second, and third specific set of sensor readings match their respective fourth, fifth, and sixth specific set of sensor readings;

in response to determining that the first, second, and third specific set of sensor readings match their respective fourth, fifth, and sixth specific set of sensor readings, predicting, by the one or more processors, that the user will re-experience the current cognitive state of the user at a future time, wherein the future time will occur after sensor readings from the first time period and the second time period are compared, wherein predicting that the user will re-experience the current cognitive state of the user at the future time is performed by:

storing the first specific set of sensor readings from the first sensor in an accumulation data matrix, wherein the first set of sensor readings are identified by the at least first "push" signal from the user of the wearable device;

storing the second specific set of sensor readings from the second sensor in the accumulation data matrix, wherein the second set of sensor readings are identified by a second "push" signal from the user of the wearable device that occurs after the first "push" signal;

storing the third specific set of sensor readings from the third sensor in the accumulation data matrix, wherein the third set of sensor readings are identified by a third "push" signal from the user of the wearable device that occurs after the second "push" signal, wherein the first specific set of sensor readings, the second specific set of sensor readings, and the third specific set of sensor readings are respectively moved from the first circular buffer, the second circular buffer, and the third circular buffer to the accumulation data matrix;

averaging corresponding blocks from the first, second, and third sensor readings in the accumulation data matrix to create averaged blocks;

storing the averaged blocks from the first, second, and third sensor readings in a push average matrix;

comparing the push average matrix to the fourth specific set of sensor readings, the fifth specific set of sensor readings, and the sixth specific set of sensor readings;

determining, by the one or more processors, that the push average matrix matches the fourth specific set of sensor readings, the fifth specific set of sensor readings, and the sixth specific set of sensor readings within a predefined range; and in response to determining that the push average matrix matches the fourth specific set of sensor readings, the fifth specific set of sensor readings, and the sixth specific set of sensor readings within a predefined range, predicting, by the one or more processors, that the user will re-experience the current cognitive state of the user at the future time; and in response to the one or more processors predicting that the user will re-experience the current cognitive state at the future time, transmitting to a smart phone, by a signal transmitter, a cognitive state signal that indicates the prediction that the user will re-experience the current cognitive state at the future time.

2. The method of claim 1, wherein the cognitive state signal is accessible only by the user.

3. The method of claim 1, further comprising:
predicting whether a particular cognitive state will occur, based on a probability formula:

$$P(M|E) = \frac{P(E|M)}{\sum m\, P(E|Mm)P(Mm)} * P(M)$$

where:
P(M|E) is a probability that a specific cognitive state will occur (M) given that (|) data from the first, second, and third circular buffers falls within a predefined Push Triggered Average (PTA) of previously pushed data from first, second, and third circular buffers;

P(E|M) is a probability that data from the first, second, and third circular buffers falls within the predefined PTA of previously pushed data from the first, second, and third circular buffers given that (|) the specific cognitive state is actually occurring (M);

P(M) is a probability that the specific cognitive state will occur regardless of any other information; and Σm is a sum of all occurrences m of the specific cognitive state, for the probability P(E|M) times the probability P(M).

4. A Cognitive Event Predictor (CEP) wearable device, wherein the CEP wearable device comprises a non-transitory computer readable storage medium having program code embodied therewith, and one or more processors for reading and executing the program code to perform a method comprising:

storing a first specific set of sensor readings from a first sensor that describe a physiological state of a user in a first circular buffer, wherein the first circular buffer is reserved for storing sensor readings from the first sensor;

storing a second specific set of sensor readings from a second sensor that describe a speech pattern of the user in a second circular buffer, wherein the second circular buffer is reserved for storing sensor readings from the second sensor;

storing a third specific set of sensor readings from a third sensor that describe an environment of the user in a third circular buffer, wherein the third circular buffer is reserved for storing sensor readings from the third sensor, wherein the first sensor, the second sensor, and the third sensor are components of a wearable device, and wherein the first, second, and third specific set of sensor readings are received during a first time period;

in response to the first sensor generating the first specific set of sensor readings, the second sensor generating the second specific set of sensor readings, and the third sensor generating the third specific set of sensor readings, prompting, by one or more processors, the user to input at least a first "push" signal on a pre-programmed key on the wearable device, wherein the first "push" signal includes a signal representing a current cognitive state of the user as identified by the user;

receiving, by a hardware receiver, the first "push" signal from the user of the wearable device, wherein the first "push" signal is transmitted by the user in response to the user subjectively experiencing the current cognitive state;

receiving a fourth specific set of sensor readings from the first sensor, wherein the fourth specific set of sensor readings are received at a second time period that is subsequent to the first time period;

receiving a fifth specific set of sensor readings from the second sensor, wherein the fifth specific set of sensor readings are received at the second time period;

receiving a sixth specific set of sensor readings from the third sensor, wherein the sixth specific set of sensor readings are received at the second time period;

comparing, by the one or more processors, the first, second, and third specific set of sensor readings to their respective fourth, fifth, and sixth specific set of sensor readings;

determining, by the one or more processors, that the first, second, and third specific set of sensor readings match their respective fourth, fifth, and sixth specific set of sensor readings;

in response to determining that the first, second, and third specific set of sensor readings match their respective fourth, fifth, and sixth specific set of sensor readings, predicting, by the one or more processors, that the user will re-experience the current cognitive state of the user at a future time, wherein the future time will occur after sensor readings from the first time period and the second time period are compared, wherein predicting that the user will re-experience the current cognitive state of the user at the future time is performed by:

storing the first specific set of sensor readings from the first sensor in an accumulation data matrix, wherein the first set of sensor readings are identified by the at least first "push" signal from the user of the wearable device;

storing the second specific set of sensor readings from the second sensor in the accumulation data matrix, wherein the second set of sensor readings are identified by a second "push" signal from the user of the wearable device that occurs after the first "push" signal;

storing the third specific set of sensor readings from the third sensor in the accumulation data matrix, wherein the third set of sensor readings are identified by a third "push" signal from the user of the wearable device that occurs after the second "push" signal, wherein the first specific set of sensor readings, the second specific set of sensor readings, and the third specific set of sensor readings are respectively moved from the first circular buffer, the second circular buffer, and the third circular buffer to the accumulation data matrix;

averaging corresponding blocks from the first, second, and third sensor readings in the accumulation data matrix to create averaged blocks;

storing the averaged blocks from the first, second, and third sensor readings in a push average matrix;

comparing the push average matrix to the fourth specific set of sensor readings, the fifth specific set of sensor readings, and the sixth specific set of sensor readings;

determining, by the one or more processors, that the push average matrix matches the fourth specific set of sensor readings, the fifth specific set of sensor readings, and the sixth specific set of sensor readings within a predefined range; and in response to determining that the push average matrix matches the fourth specific set of sensor readings, the fifth specific set of sensor readings, and the sixth specific set of sensor readings within a predefined range, predicting, by the one or more processors, that the user will re-experience the current cognitive state of the user at the future time; and in response to the one or more processors predicting that the user will re-experience the current cognitive state at the future time, transmitting to a smart phone, by a signal transmitter, a cognitive state signal that indicates the prediction that the user will re-experience the current cognitive state at the future time.

5. A computer program product comprising a computer readable storage medium having program code embodied therewith, the program code readable and executable by a processor to perform method comprising:

storing a first specific set of sensor readings from a first sensor that describe a physiological state of a user in a first circular buffer, wherein the first circular buffer is reserved for storing sensor readings from the first sensor;

storing a second specific set of sensor readings from a second sensor that describe a speech pattern of the user in a second circular buffer, wherein the second circular buffer is reserved for storing sensor readings from the second sensor;

storing a third specific set of sensor readings from a third sensor that describe an environment of the user in a third circular buffer, wherein the third circular buffer is reserved for storing sensor readings from the third sensor, wherein the first sensor, the second sensor, and the third sensor are components of a wearable device, and wherein the first, second, and third specific set of sensor readings are received during a first time period;

in response to the first sensor generating the first specific set of sensor readings, the second sensor generating the second specific set of sensor readings, and the third sensor generating the third specific set of sensor readings, prompting, by one or more processors, the user to input at least a first "push" signal on a pre-programmed key on the wearable device, wherein the first "push" signal includes a signal representing a current cognitive state of the user as identified by the user;

receiving, by a hardware receiver, the first "push" signal from the user of the wearable device, wherein the first "push" signal is transmitted by the user in response to the user subjectively experiencing the current cognitive state;

receiving a fourth specific set of sensor readings from the first sensor, wherein the fourth specific set of sensor readings are received at a second time period that is subsequent to the first time period;

receiving a fifth specific set of sensor readings from the second sensor, wherein the fifth specific set of sensor readings are received at the second time period;

receiving a sixth specific set of sensor readings from the third sensor, wherein the sixth specific set of sensor readings are received at the second time period;

comparing, by the one or more processors, the first, second, and third specific set of sensor readings to their respective fourth, fifth, and sixth specific set of sensor readings;

determining, by the one or more processors, that the first, second, and third specific set of sensor readings match their respective fourth, fifth, and sixth specific set of sensor readings;

in response to determining that the first, second, and third specific set of sensor readings match their respective fourth, fifth, and sixth specific set of sensor readings, predicting, by the one or more processors, that the user will re-experience the current cognitive state of the user at a future time, wherein the future time will occur after sensor readings from the first time period and the second time period are compared, wherein predicting that the user will re-experience the current cognitive state of the user at the future time is performed by:

storing the first specific set of sensor readings from the first sensor in an accumulation data matrix, wherein the first set of sensor readings are identified by the at least first "push" signal from the user of the wearable device;

storing the second specific set of sensor readings from the second sensor in the accumulation data matrix, wherein the second set of sensor readings are identified by a second "push" signal from the user of the wearable device that occurs after the first "push" signal;

storing the third specific set of sensor readings from the third sensor in the accumulation data matrix, wherein the third set of sensor readings are identified by a third "push" signal from the user of the wearable device that occurs after the second "push" signal, wherein the first specific set of sensor readings, the second specific set of sensor readings, and the third specific set of sensor readings are respectively moved from the first circular buffer, the second circular buffer, and the third circular buffer to the accumulation data matrix;

averaging corresponding blocks from the first, second, and third sensor readings in the accumulation data matrix to create averaged blocks;

storing the averaged blocks from the first, second, and third sensor readings in a push average matrix;

comparing the push average matrix to the fourth specific set of sensor readings, the fifth specific set of sensor readings, and the sixth specific set of sensor readings;

determining, by the one or more processors, that the push average matrix matches the fourth specific set of sensor readings, the fifth specific set of sensor readings, and the sixth specific set of sensor readings within a predefined range; and in response to determining that the push average matrix matches the fourth specific set of sensor readings, the fifth specific set of sensor readings, and the sixth specific set of sensor readings within a predefined range, predicting, by the one or more processors, that the user will re-experience the current cognitive state of the user at the future time; and in response to the one or more processors predicting that the user will re-experience the current cognitive state at the future time, transmitting to a smart phone, by a signal transmitter, a cognitive state signal that indicates the prediction that the user will re-experience the current cognitive state at the future time.

6. The computer program product of claim 5, wherein the first sensor and the second sensor detect a walking gait of the user.

7. The computer program product of claim 5, wherein the method further comprises:

predicting whether a particular cognitive state will occur, based on a probability formula:

$$P(M \mid E) = \frac{P(E \mid M)}{\sum m\, P(E \mid Mm) P(Mm)} * P(M)$$

where:

P(M|E) is a probability that a specific cognitive state will occur (M) given that (|) data from the first, second, and third circular buffers falls within a predefined Push Triggered Average (PTA) of previously pushed data from the first, second, and third circular buffers;

P(E|M) is a probability that data from the first, second, and third circular buffers falls within the predefined PTA of previously pushed data from the first, second, and third circular buffers given that (|) the specific cognitive state is actually occurring (M);

P(M) is a probability that the specific cognitive state will occur regardless of any other information; and Σm is a sum of all occurrences m of the specific cognitive state, for the probability P(E|M) times the probability P(M).

\* \* \* \* \*